US012006125B2

(12) United States Patent
Hutterer et al.

(10) Patent No.: US 12,006,125 B2
(45) Date of Patent: Jun. 11, 2024

(54) CONTAINER FOR PACKAGING UNITS

(71) Applicants: Gerresheimer Glas GmbH, Düsseldorf (DE); Stevanato Group S.p.A., Piombino Dese (IT)

(72) Inventors: Nicole Hutterer, Wackersdorf (DE); Andreas Fraas, Amberg (DE); Ricardo Colchado, Corregidora (MX); Stephen Flynn, Peachtree City, GA (US); Braden Miller, Havertown, PA (US); Scott Rosenman, Mount Laurel, NJ (US); Alessio Bonati, Cadoneghe (IT); Michele Guasti, Treviso (IT); Marco Canestraro, Carmignano di Brenta (IT); Riccardo Prete, Ponte San Nicolo (IT); Gianpaolo Bertolin, Noale (IT)

(73) Assignees: Gerresheimer Glas GmbH, Düsseldorf (DE); Stevanato Group S.p.A., Piombino Dese (IT)

( * ) Notice: Subject to any disclaimer, the term of this patent is extended or adjusted under 35 U.S.C. 154(b) by 0 days.

(21) Appl. No.: 17/746,554

(22) Filed: May 17, 2022

(65) Prior Publication Data
US 2022/0371807 A1    Nov. 24, 2022

Related U.S. Application Data

(60) Provisional application No. 63/190,089, filed on May 18, 2021.

(51) Int. Cl.
*A61J 1/16*    (2023.01)
*A61M 5/00*    (2006.01)
(Continued)

(52) U.S. Cl.
CPC .............. *B65D 81/263* (2013.01); *A61J 1/16* (2013.01); *A61M 5/002* (2013.01); *B65B 5/06* (2013.01);
(Continued)

(58) Field of Classification Search
CPC ...... B65D 81/263; B65D 1/26; B65D 25/108; B65D 77/2024; A61J 1/16; A61M 5/002
(Continued)

(56) References Cited

U.S. PATENT DOCUMENTS 2,702,647 A    2/1955    Wesling
4,105,407 A    8/1978    Sanderson
(Continued)

FOREIGN PATENT DOCUMENTS

CN    1726148    1/2006
CN    101237896    8/2008
(Continued)

OTHER PUBLICATIONS

Atkins, Nick, "Sterile Ready-to-Fill Components | Adelphi Healthcare Packaging", Nov. 28, 2012, pp. 1-1, Retrieved from the Internet: URL: https://adelphi-hp.com/news-events/sterile-ready-to-fill%C2%AE-components [retrieved on Sep. 23, 2022].
(Continued)

*Primary Examiner* — Steven A. Reynolds
(74) *Attorney, Agent, or Firm* — Fish & Richardson P.C.

(57) ABSTRACT

The present disclosure describes a container that includes a body having a lower surface, an upper rim, and a plurality of side walls that extend between the lower surface and the upper rim, wherein the upper rim defines an opening to an interior space of the body, a flexible cover that covers the opening of the body and is bonded to the body along the upper rim, and gas-permeable material through which gas can enter and exit the interior space of the body. The upper
(Continued)

rim of the body is spaced apart from any of the gas-permeable material, such that the cover can be peeled away from the upper rim to expose the opening while leaving the gas-permeable material intact.

5 Claims, 8 Drawing Sheets

(51) Int. Cl.
| | | |
|---|---|---|
| B65B 5/06 | (2006.01) | |
| B65B 7/28 | (2006.01) | |
| B65B 55/02 | (2006.01) | |
| B65D 1/26 | (2006.01) | |
| B65D 25/10 | (2006.01) | |
| B65D 77/20 | (2006.01) | |
| B65D 81/26 | (2006.01) | |

(52) U.S. Cl.
CPC ............... *B65B 7/28* (2013.01); *B65B 55/02* (2013.01); *B65D 1/26* (2013.01); *B65D 25/108* (2013.01); *B65D 77/2024* (2013.01); *A61M 2207/00* (2013.01)

(58) Field of Classification Search
USPC .................................................. 206/539, 438
See application file for complete search history.

(56) References Cited

U.S. PATENT DOCUMENTS

| | | | |
|---|---|---|---|
| 4,457,432 A | 7/1984 | Solheim | |
| 5,080,222 A | 1/1992 | McNary | |
| 5,372,787 A * | 12/1994 | Ritter | A61B 50/30 206/508 |
| 7,300,637 B2 | 11/2007 | Lin et al. | |
| 7,708,142 B2 | 5/2010 | Ehrlund | |
| 8,679,404 B2 * | 3/2014 | Liburd | A61F 2/0095 206/439 |
| 9,918,898 B2 | 3/2018 | Fadeev et al. | |
| 9,938,042 B1 | 4/2018 | Aryanpanah et al. | |
| 10,017,294 B2 | 7/2018 | Deutschle et al. | |
| 10,703,539 B2 | 7/2020 | Deutschle et al. | |
| 2002/0022246 A1 | 2/2002 | Lin et al. | |
| 2003/0091471 A1 | 5/2003 | Lacabanne | |
| 2003/0183547 A1* | 10/2003 | Heyman | A61L 2/26 206/439 |
| 2003/0199082 A1 | 10/2003 | Miller et al. | |
| 2008/0236631 A1 | 10/2008 | Lin et al. | |
| 2008/0317912 A1 | 12/2008 | Keller et al. | |
| 2011/0094901 A1 | 4/2011 | Ingvardsen et al. | |
| 2011/0296800 A1 | 12/2011 | Clark et al. | |
| 2013/0280134 A1 | 10/2013 | Hoffman et al. | |
| 2014/0027326 A1 | 1/2014 | Peruzzo | |
| 2014/0216059 A1 | 8/2014 | Moore et al. | |
| 2016/0288126 A1 | 10/2016 | Motadel et al. | |
| 2017/0073091 A1 | 3/2017 | Deutschle et al. | |
| 2017/0225162 A1 | 8/2017 | Liu et al. | |
| 2017/0247132 A1 | 8/2017 | Deutschle et al. | |
| 2017/0333938 A1 | 11/2017 | Brennan et al. | |
| 2018/0057249 A1* | 3/2018 | Bertolin | B65D 85/42 |
| 2018/0116907 A1 | 5/2018 | Fadeev et al. | |
| 2018/0208377 A1 | 7/2018 | Kloke et al. | |
| 2019/0083697 A1 | 3/2019 | Evans et al. | |
| 2019/0299217 A1 | 10/2019 | Motadel et al. | |
| 2019/0343721 A1 | 11/2019 | Komann et al. | |
| 2020/0246223 A1 | 8/2020 | Nicolas et al. | |
| 2022/0371760 A1 | 11/2022 | Redeker et al. | |
| 2022/0371762 A1 | 11/2022 | Rosenman et al. | |
| 2022/0371765 A1 | 11/2022 | Hutterer et al. | |
| 2022/0371773 A1 | 11/2022 | Hutterer et al. | |
| 2022/0371781 A1 | 11/2022 | Hutterer et al. | |

FOREIGN PATENT DOCUMENTS

| | | |
|---|---|---|
| CN | 101272811 | 9/2008 |
| CN | 104271346 | 1/2015 |
| CN | 104755604 | 7/2015 |
| CN | 106347771 | 1/2017 |
| CN | 106458416 | 2/2017 |
| CN | 106998715 | 8/2017 |
| CN | 108473247 | 8/2018 |
| DE | 2952733 | 7/1981 |
| DE | 9112325 | 11/1991 |
| DE | 202012010704 | 12/2012 |
| DE | 102013114404 A1 | 6/2015 |
| DE | 102020206748 | 12/2020 |
| EP | 0903176 | 3/1999 |
| EP | 1780143 | 5/2007 |
| EP | 2408483 | 1/2012 |
| EP | 2543391 | 3/2016 |
| EP | 3345587 | 7/2018 |
| JP | 2001112857 | 4/2001 |
| WO | WO 2010/106168 | 9/2010 |
| WO | WO 2011/135085 | 11/2011 |
| WO | WO 2014/130349 | 8/2014 |
| WO | WO 2015/076780 | 5/2015 |
| WO | WO 2017/044906 | 3/2017 |
| WO | WO 2018/175985 | 9/2018 |

OTHER PUBLICATIONS

Lavajo Nathalie et al: "Specifications—Vials and bottles for parenteral application Code: PC-00132 Revision: 08 Specifications Vials and bottles for parenteral application: Injectables Infusions Approval cycle", Oct. 16, 2019, pp. 1-25, Retrieved from the Internet: URL:https://www.sgd-pharma.com/sites/default/files/mediacenter/pc-00132_08_-_specifications_-_parenteral_application_vials_and_bottles_0.pdf [retrieved on Mar. 24, 2023].

Le Printing Machine Factory Limited: "How to Manufacture Glass Bottles", Sep. 10, 2016, Retrieved from the Internet: URL:https://www.youtube.com/watch?v=hGjYRaYjryI [retrieved on Mar. 24, 2023].

Manufacturing Chemist Redactor: "Pure, smooth and strong", Apr. 16, 2021, pp. 1-10, Retrieved from the Internet: URL:https://www.manufacturingchemist.com/news/article_page/Pure_smooth_and_strong/175981 [retrieved on Mar. 24, 2023].

Extended European Search Report in European Appln No. 22174016.0, dated Oct. 17, 2023, 9 pages.

Schott: "EVERIC smooth", Jan. 17, 2020, Retrieved from the Internet: URL:https://www.youtube.com/watch?v=niHtVIYbQaM [retrieved on Jun. 30, 2023].

Wang, "Science of Packaging Materials," China Light Industry Press, Feb. 28, 2017, pp. 188-189.

CN Office Action in Chinese Appln. No. 202210538013.9, dated Jan. 21, 2024, 15 pages (with English translation).

\* cited by examiner

CONTAINER FOR PACKAGING UNITS

CROSS-REFERENCE TO RELATED APPLICATION

This application claims the benefit of priority to U.S. Provisional Patent Application No. 63/190,089, filed on May 18, 2021, the entire contents of which are incorporated by reference herein.

BACKGROUND

This disclosure relates to a container for storing and transporting packaging units and a method for making such a container.

Containers are used for various purposes. For example, a container can be used to store and transport several smaller containers or packaging units during an industrial process. Such packaging units can include vials, cartridges, ampoules, bottles, or pre-Tillable syringes. In many industries, these different types of packaging units are collectively known as "primary packaging," i.e., the packaging that comes into direct contact with an end product. The end product may be a food product, a cosmetic product, or a pharmaceutical product. Thus, the container can serve as "secondary packaging," i.e., packaging that groups, protects, and labels the primary packaging.

Primary packaging can sometimes be sterilized while still inside the secondary packaging. Generally speaking, sterilization processes use heat, chemicals, or radiation to kill microorganisms, such as bacteria or fungi. Accordingly, containers that serve as secondary packaging can include features that allow sterilant to enter the container and come into contact with the primary packaging stored inside.

U.S. Pat. No. 10,017,294 B2 describes a transport and packaging container, in which containers are accommodated without an additional supporting structure, i.e. directly. An upper segment is formed in the manner of a drawer having a bottom, two lateral side walls, and a rear side wall, both of which protrude at right angles from the bottom. Circular openings are formed in the side walls, which can be sterile sealed by a protective foil, such as a meshwork of synthetic fibers such as polypropylene fibers (PP) or a Tyvek® protective foil.

US 2014/0027326 A1 describes a tub having a body able to contain a nest and medical containers, which has an inner shoulder for receiving the nest. The tub has an upper peripheral wall delineating an upper opening and including a peripheral outer flange leveled with this upper opening, for the sealing of the sealing cover. The tub is integrally formed by a single part of molded plastic material. The sealing cover is formed by a sheet of suitable heat sealable material, in particular by a sheet in Tyvek®, and is sealed on the upper peripheral wall or on the outer flange of the tub by heat welding.

SUMMARY

Aspects of the present disclosure aim to alleviate problems associated with known containers.

According to a first general aspect of the present disclosure, a container includes a body that includes a lower surface, an upper rim, and a plurality of side walls that extend between the lower surface and the upper rim, wherein the upper rim defines an opening to an interior space of the body, a flexible cover that covers the opening of the body and is bonded to the body along the upper rim, and gas-permeable material through which gas can enter and exit the interior space of the body. The upper rim of the body is spaced apart from any of the gas-permeable material, such that the cover can be peeled away from the upper rim to expose the opening while leaving the gas-permeable material intact.

The gas-permeable material may include an insert formed in the flexible cover, and the flexible cover may include a gas-impermeable material that encircles the insert.

Alternatively, the entire flexible cover may be formed of a gas-impermeable material.

One of the plurality of side walls may include one or more apertures that extend through the side wall and that are covered by the gas-permeable material.

More specifically, a first side wall may include one or more first apertures that extend through the first side wall and are covered by the gas-permeable material, and a second side wall opposite the first side wall may include one or more second apertures that extend through the second side wall and are covered by the gas-permeable material.

In some cases, all of the side walls may include one or more apertures that are covered by the gas-permeable material.

The lower surface may include one or more apertures that extend through the lower surface and that are covered by the gas-permeable material.

The one or more apertures in the lower surface may be provided in addition to or in lieu of any apertures in the side wall(s).

The one or more apertures in the lower surface may align with one or more gas-permeable inserts that may be provided in the flexible cover.

The container may also include a support tray that is arranged in the interior space of the body and includes an array of recesses, each recess configured to receive a vial, ampoule, cartridge, or syringe body. The support tray is sized to fit through the opening of the body.

According to a second general aspect of the present disclosure, a method includes receiving a body that includes a lower surface, an upper rim, and a plurality of side walls that extend between the lower surface and the upper rim, wherein the upper rim defines an opening to an interior space of the body, and wherein one of the plurality of side walls includes one or more apertures that extend through the side wall and/or the lower surface includes one or more apertures that extend through the lower surface, and covering the one or more apertures with a gas-permeable material.

Covering the one or more apertures with a gas-permeable material can include bonding the gas-permeable material to an outer surface of the side wall. In other instances, covering the one or more apertures with a gas-permeable material includes attaching the gas-permeable material during an injection molding process to form the body. In other words, the gas-permeable material can be attached during the manufacturing process of the body or afterwards in a separate step.

The method can further include loading a plurality of vials, ampoules, cartridges, or syringe bodies in corresponding recesses of a support tray, arranging the loaded support tray in the interior space of the body, and bonding a flexible cover to the body along the upper rim of the body. The flexible cover can include a gas-permeable insert encircled by a gas-impermeable material.

Alternatively, the entire flexible cover may be formed of a gas-impermeable material.

A flexible cover that includes a gas-permeable insert can be made in several ways. For example, the method can include receiving a flexible cover made of gas-impermeable material that is sized to cover the opening to the interior space of the body, forming an opening in the gas-impermeable material, covering the opening in the gas-impermeable material with a gas-permeable insert, and bonding a peripheral edge of the gas-impermeable material to the upper rim of the body. The gas-permeable insert can be adhered to the gas-impermeable material using an adhesive. In some cases, the gas-impermeable material is a first layer of gas-impermeable material, and the method may include arranging a second layer of gas-impermeable material over the gas-permeable insert, wherein the second layer of gas-impermeable material includes an opening aligned with the gas-permeable insert, and laminating the gas-permeable insert between the first and second layers of gas-impermeable material.

These and other embodiments described herein may provide one or more of the following benefits. Firstly, gas-permeable material may have a tendency to generate particles that can cling to and potentially contaminate the contents of the container. The container according to the disclosure may reduce the amount of gas-permeable material and, therefore, the potential to generate such particles. Secondly, gas-permeable material may be particularly prone to particle generation when manipulated in certain ways. By leaving any and all gas-permeable material intact, the container may further reduce unwanted particle generation. With the likelihood of particle generation reduced, the flexible cover may be removed more quickly. Finally, certain configurations of gas-permeable material in the container may improve the sterilization process by providing an entrance and exit for gaseous sterilant. When placed under vacuum pressure, the entrance and exit may improve the flow of sterilant through the container, and thus improve the efficiency of the sterilization process.

DESCRIPTION OF THE DRAWINGS

Certain embodiments will now be described, by way of example only, with reference to the accompanying drawings, in which.

Like reference numbers and designations in the various drawings indicate like elements.

DETAILED DESCRIPTION

Figure 1:
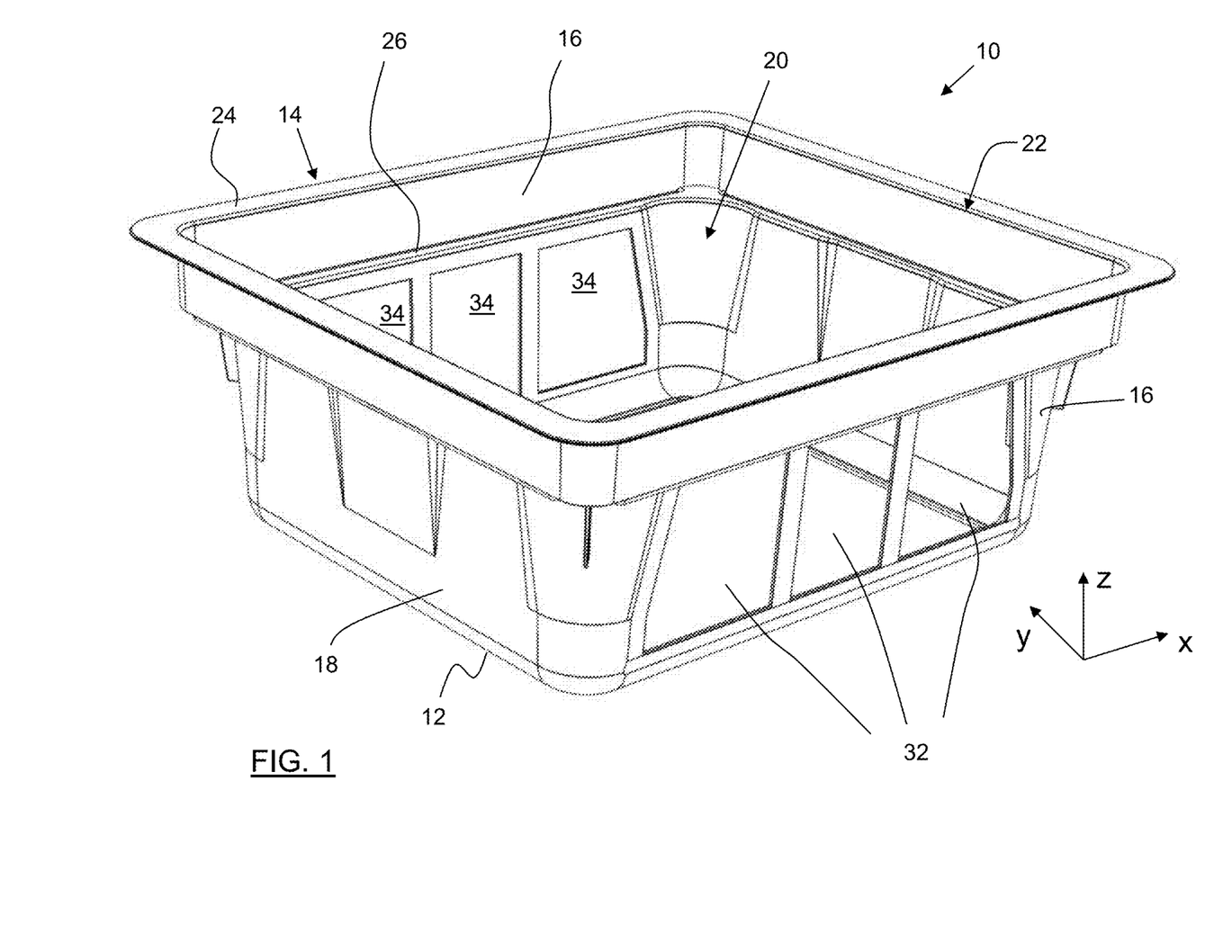
FIG. 1 shows an example of a body for a container according to the present disclosure.

FIG. 1 shows a body 10 for a container 100 according to the present disclosure. The body 10 may be referred to as a "tub" and can be used as secondary packaging for primary packaging in the food, cosmetic, or pharmaceutical industries. Although the expression "primary packaging" can encompass vials, cartridges, ampoules, bottles, and syringes to name a few examples, the following description will refer to "vials" for all types of primary packaging.

The body 10 includes a lower surface 12, an upper rim 14, and side walls 16, 18 that extend between the lower surface 12 and the upper rim 14. The lower surface 12 can be a flat planar surface that rests on a table or worktop (not shown). As illustrated, the lower surface 12 has a rectangular shape with two long edges and two short edges. Accordingly, the side walls 16, 18 include an opposing pair of long side walls 16 and an opposing pair of short side walls 18. Referring to the coordinate axes shown in FIG. 1, each long side wall 16 extends along the X-axis and a corresponding long edge of the lower surface 12. Each short side wall 18 extends along the Y-axis and a corresponding short edge of the lower surface 12. All four side walls 16, 18 extend in the vertical direction, along the Z-axis, to connect the lower surface 12 and the upper rim 14. Together, the lower surface 12 and the side walls 16, 18 define an interior space 20 of the body 10 that can receive, e.g., a set of vials to be filled with a pharmaceutical product.

The upper rim 14 defines an opening 22 to the interior space 20 of the body 10. As illustrated in FIG. 1, the rim 14 can include a lip or flange 24 that encloses the opening 22 to the interior space 20. The flange 24 can extend in a plane defined by the X-Y-axes, substantially orthogonally to the side walls 16, 18. As described below, the flange 24 can serve as a point of attachment for a cover (not shown in FIG. 1).

The opening 22 can be sized to accommodate a support tray or "nest" that supports the primary packaging within the interior space 20 of the body 10 (not shown). The support tray can include an array of recesses that are each sized to receive a vial. The support tray can ensure that the vials are securely supported in an upright position and do not come into contact with one another. For example, an empty support tray can be inserted through the opening 22 of the interior space 20. In some cases, a peripheral edge of the support tray can rest on an inner shoulder 26 that extends along some or all of the side walls 16, 18. Individual vials can be arranged in the respective openings of the support tray. In some cases, the vials are individually placed in the interior space 20 of the body 10 without any kind of support tray.

Figure 2:
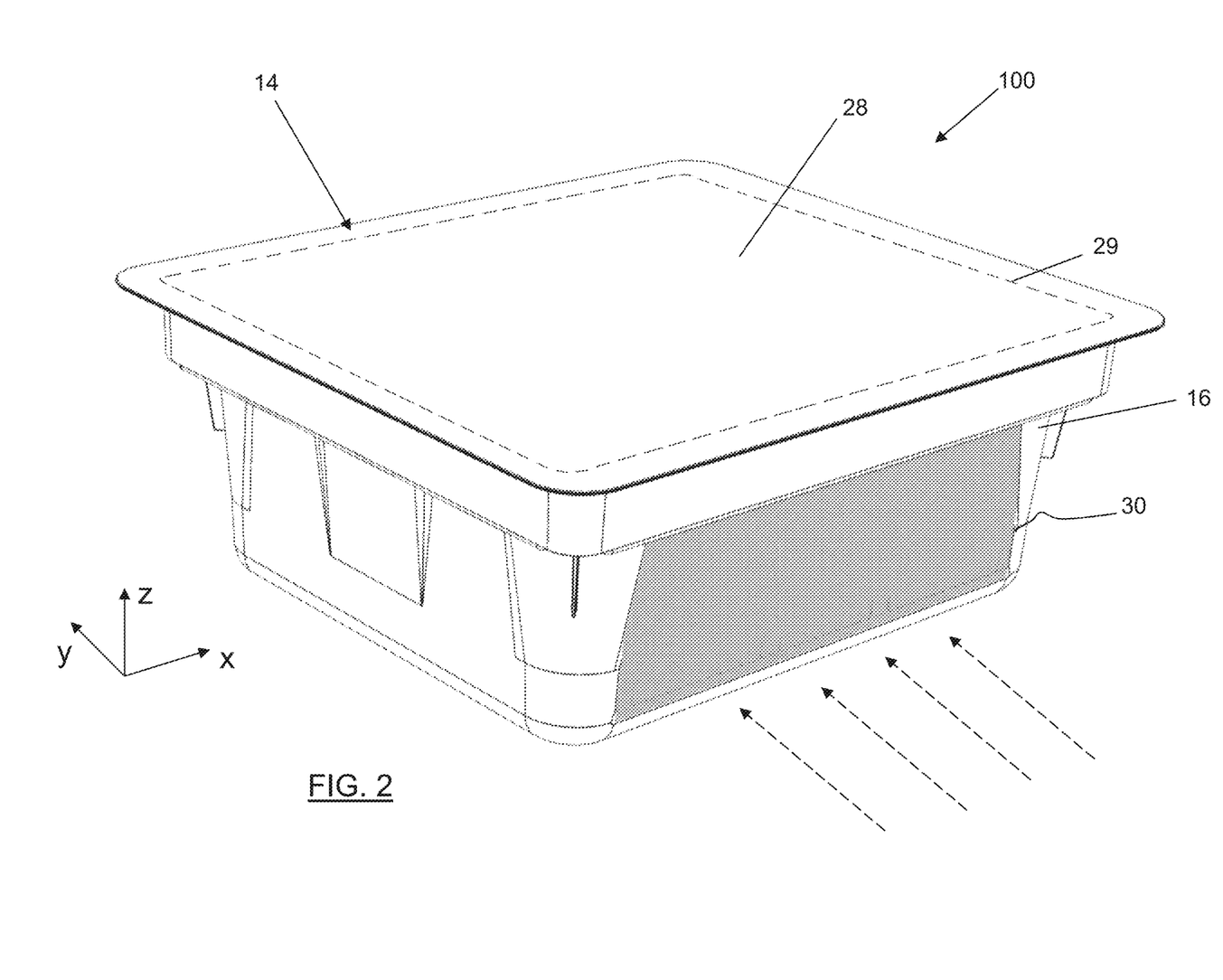
FIGS. 2 to 4 each show an example of a container according to the present disclosure.

After the vials are loaded into the interior space of the body 10, a flexible cover 28 is bonded to the body 10 along the upper rim 14, as shown in FIG. 2. For example, the flexible cover 28 can be heat sealed to the flange 24 of the rim along a peripheral seam 29. The flexible cover 28 covers the opening 22 of the body 10 and thus isolates the interior space 20 defined by the body 10. In other words, the flexible cover 28 seals the vials inside the body 10. The sealed package or container 100 can be used to securely store and transport the vials. For example, the vials can be sterilized while inside of the container 100.

During sterilization, several filled containers 100 can be loaded into a sterilization chamber that places the containers 100 under a vacuum. For example, the containers 100 and vials can be exposed to a gaseous chemical sterilant, such as ethylene oxide, nitrogen dioxide, or ozone. The sterilant can enter the container 100 through a gas-permeable material 30, as depicted by the dashed arrows in FIG. 2. In the present disclosure, the container 100 can include several, discrete pieces of gas-permeable material that are collectively referred to as "the gas-permeable material." The gas-permeable material 30 is shown as a single sheet of material adhered to an outer surface of a long side wall 16. The sheet of gas-permeable material 30 covers three windows or apertures 32 that are formed in and extend through the long side wall 16 (FIG. 1). The combination of apertures 32 and gas-permeable material 30 allow the gaseous sterilant to enter and exit the interior space 20 of the body 10, and thus, the container 100.

Figure 3:
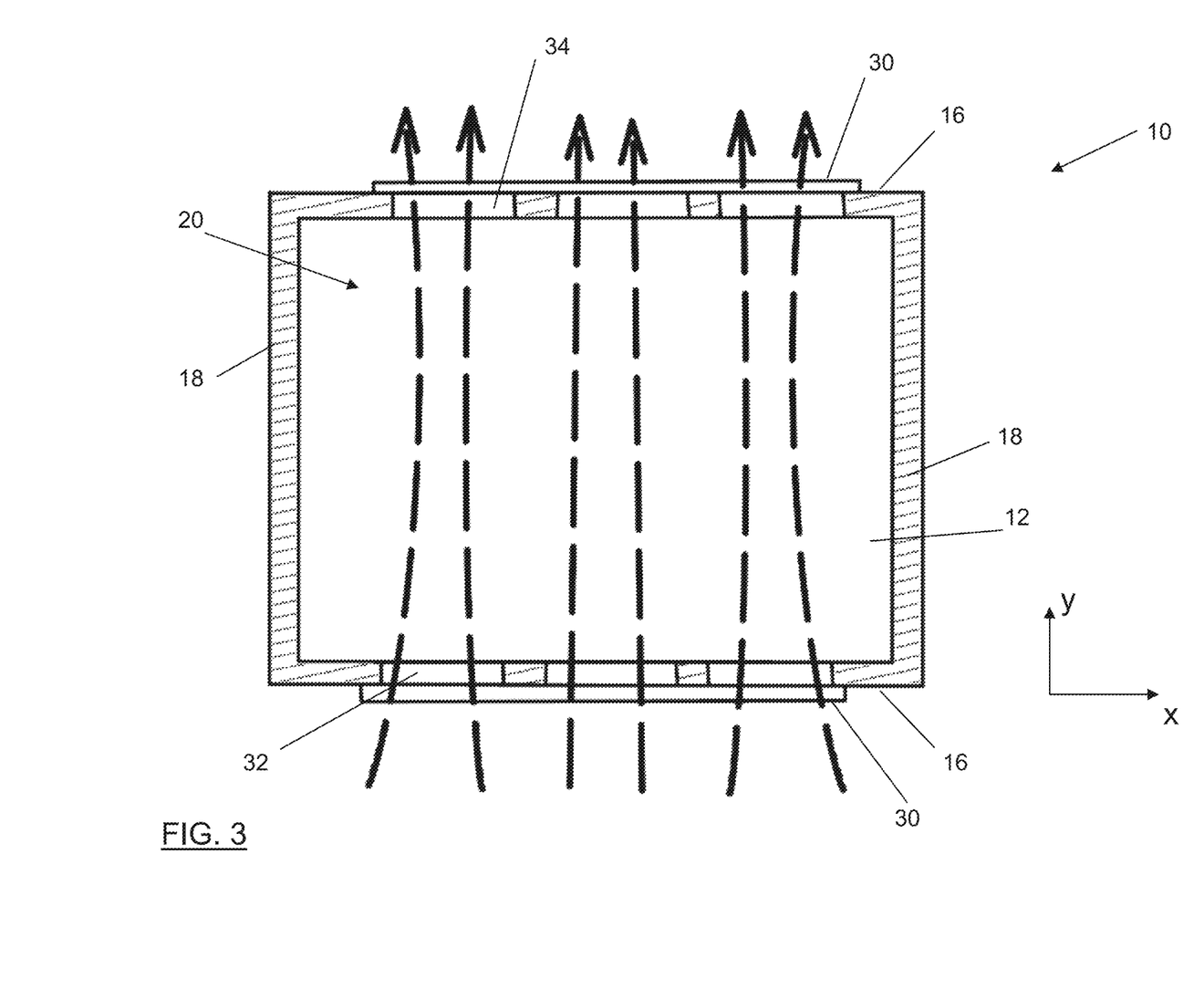

Referring to FIGS. 1 and 3, each of the apertures 32 in the long side wall 16 are aligned along the Y-axis with a corresponding aperture 34 in the opposite long side wall 16. The apertures 34 are also covered by a sheet of gas-permeable material 30 that allows gaseous sterilant to enter and exit the interior space 20 of the body 10. When placed under a vacuum in the sterilization chamber, the opposing apertures 32, 34 may create a pressure differential that induces a flow of gaseous sterilant (shown by the dashed arrows) through the interior space 20 of the body 10. As illustrated, the opposing apertures 32, 34 are aligned, i.e., fully overlap along the Y-axis to induce the paths represented by the dashed arrows. However, in some cases, the apertures may not be aligned along any of the coordinate axes shown in the Figures. For example, an aperture may be formed at one end of a first side wall, and a second aperture may be formed at an opposite end of an opposing side wall. The first and second apertures may form an entrance and exit for the gaseous sterilant through the interior space of the body and container.

In FIGS. 1 to 3, the opposing apertures 32, 34 are formed in the long side walls 16. However, the apertures may be formed elsewhere in the container 100. For example, pairs of opposing apertures can be formed in both the long side walls 16 and the short side walls 18. Further, the apertures 32, 34 may not necessarily be formed in opposing pairs. In some cases, an aperture may be provided in one surface of the container 100 while the opposing surface is continuously formed, i.e., free from apertures.

The gas-permeable material 30 can include a gas-permeable foil, such as Tyvek®. Tyvek is a non-woven material formed of high-density polyethylene fibers that is permeable to gas and water vapor but not to liquids. Although FIGS. 1 to 3 show a single continuous sheet of gas-permeable material 30 attached to each of the long side walls 16, the gas-permeable material 30 can also be cut to size to cover individual apertures 32, 34. As described below in more detail, the gas-permeable material 30 can be applied to the body 10 when the body 10 is manufactured. Alternatively, the gas-permeable material 30 can be applied to the body 10 at a later time, for example, shortly before the vials are packaged in the container 100.

Figure 4:
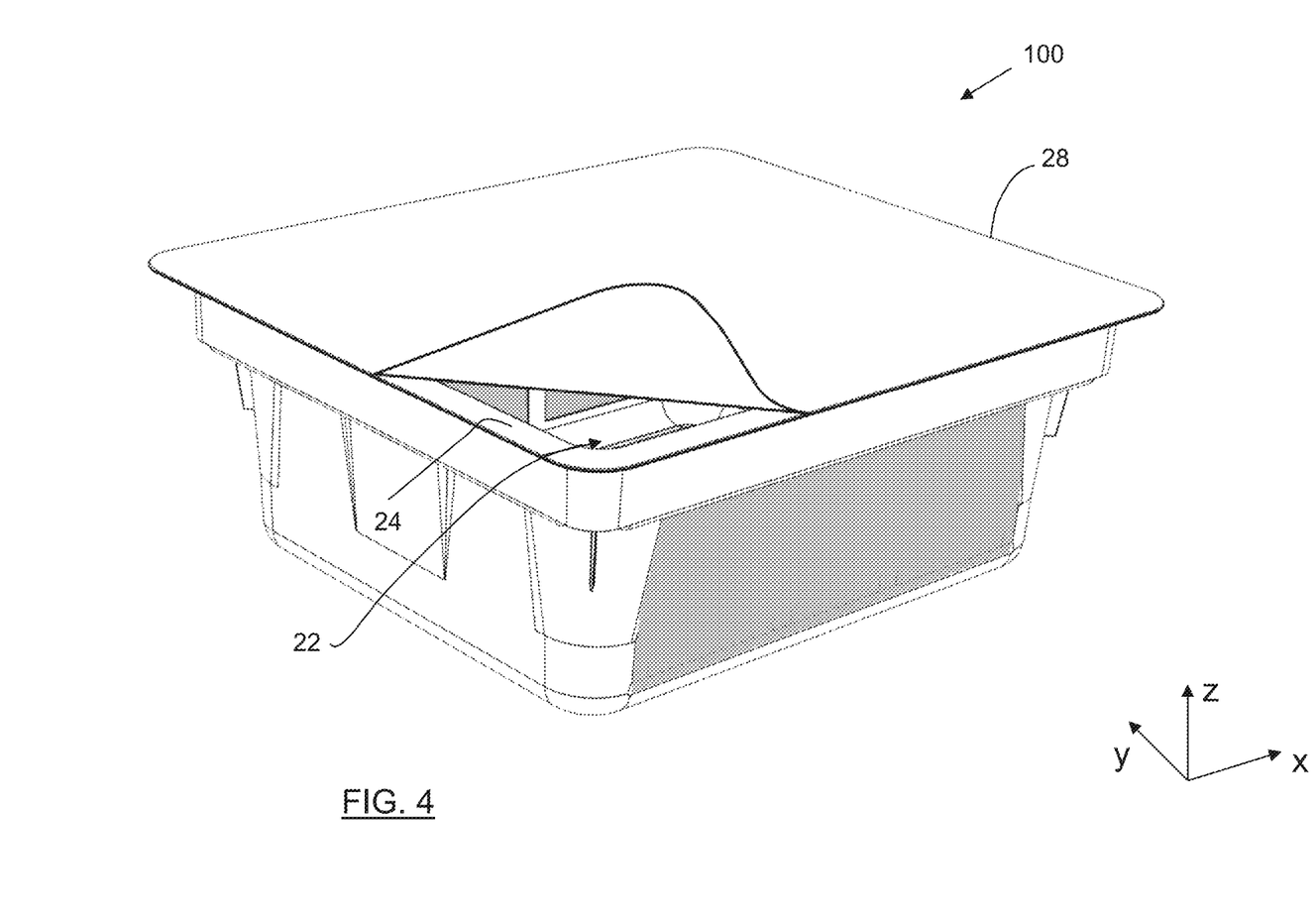

Once the sterilization process is complete, the entire container 100 can be placed in a flexible or rigid bag to maintain sterility (not shown). When the time comes to use the sterile vials, the flexible cover 28 can be peeled from the flange 24, as shown in FIG. 4. For example, the flexible cover 28 can be peeled by breaking the bond between the flange 24 and the flexible cover 28 along the peripheral seam 29 shown, e.g., in FIG. 2.

Peeling the flexible cover 28 away from the rim 14 and the flange 24 exposes the opening 22 to the interior space 20 of the body 10. In accordance with the present disclosure, the upper rim 14 is spaced away from any of the gas-permeable material 30, such that the flexible cover 28 can be peeled away from the upper rim 14 while leaving the gas-permeable material 30 intact. In this context, "spaced away" can include that neither the upper rim 14 nor the peripheral seam 29 comes into contact with any of the gas-permeable material 30 provided in the container 100. Gas-permeable material 30 may generate particles when manipulated in certain ways. By leaving the gas-permeable material 30 intact as the flexible cover 28 is peeled from the upper rim 14, the generation of particles can be reduced. Reduced particle generation reduces the exposure of the vials stored in the container 100 to such particles.

The upper rim 14 can be spaced away from the gas-permeable material 30 in a number of ways. For example, the flexible cover 28 can be free from gas-permeable material, i.e., made of gas-impermeable material. In this case, the flexible material 30 may be located only on the side walls 16, 18 or the lower surface 12 of the body and remain intact, namely attached to the body 10, as the flexible cover 28 is peeled from the upper rim 14. Examples of gas-impermeable materials that are suitable for the flexible cover 28 include rigid or semi-rigid plastic, a low-density polyethylene (LDPE) film, or a polyethylene film laminated with a polyethylene terephthalate film (PE/PET bi-layer film).

Figure 5:
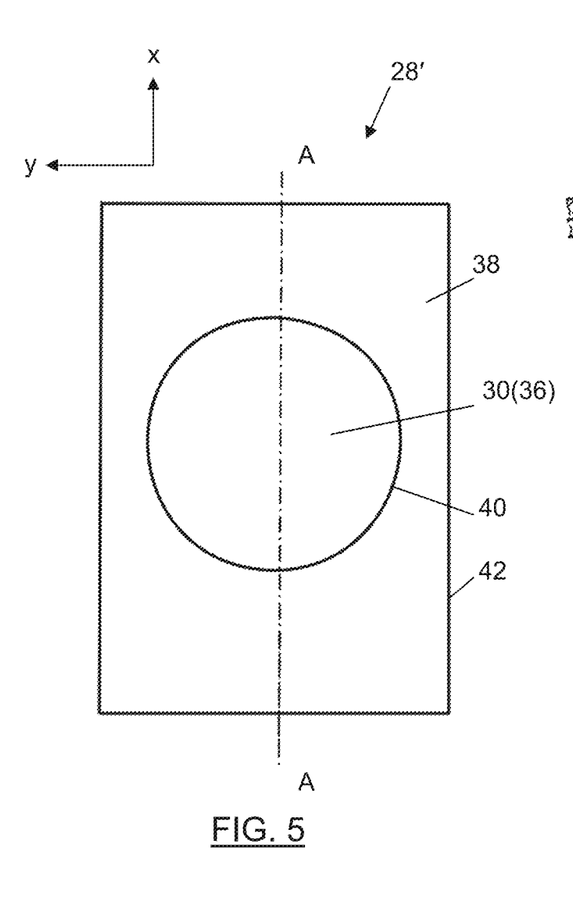
FIG. 5 shows an example of a flexible cover.

Another way in which the upper rim 14 can be spaced away from the gas-permeable material 30 is show in FIG. 5. More specifically, the gas-permeable material 30 provided in the container 100 can include an insert 36 formed in the flexible cover 28'. The flexible cover 28' also includes a gas-impermeable material 38 that encircles the insert 36. In this instance, "encircles" may mean that the gas-impermeable material 38 surrounds a peripheral edge of the insert 36 while leaving the top and bottom surfaces of the insert 36 free for gas to travel through the insert 36. Although the insert 36 is shown as having a circular shape, the insert 36 may also be square or rectangular in some instances. Accordingly, the expression "encircles" does not necessitate a circular insert 36.

The insert 36 and the gas-impermeable material 38 are designed with a distance between a peripheral edge 40 of the insert 36 and a peripheral edge 42 of the flexible cover 28' that allows the peripheral seam 29 (not shown) to be formed along the peripheral edge 42 of the flexible cover 28 without overlapping the insert 36 formed of gas-permeable material 30. Due to the distance between the peripheral seam 29 and the insert 36, the flexible cover 28' can be peeled away from the upper rim to expose the opening while leaving the gas-permeable material 30 intact.

In some instances, the insert 36 in the flexible cover 28' can be aligned with an aperture that is formed in the lower surface 12 of the body and covered by a further sheet of gas-permeable material 30. For example, the insert 36 and the aperture can be aligned along the Z-axis shown in the figures. The insert 36 and the aperture in the lower surface 12 form an opposing pair of openings that induce flow of the gaseous sterilant similarly to the apertures 32, 34 shown in FIG. 3. Although the flexible cover 28' is shown with a single insert 36, multiple inserts can be formed across the surface of the flexible cover 28' to evenly distribute the flow of gaseous sterilant and reduce regions of so-called "dead space" inside the container 100. In such a case, each smaller insert is nonetheless encircled by the gas-impermeable material 38.

Figure 6A:
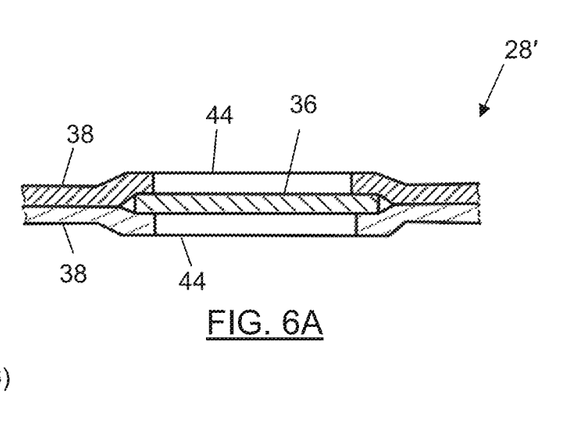
FIGS. 6A and 6B show example cross-sections of the flexible cover of FIG. 5.
Figure 6B:
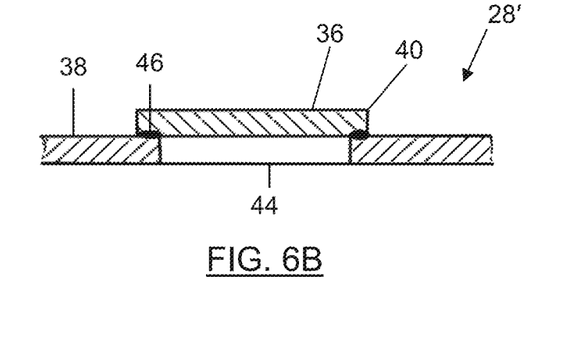

FIGS. 6A and 6B show two ways of making the flexible cover 28' shown in FIG. 5. In FIG. 6A, the flexible cover 28' includes a gas-permeable insert 36 that is laminated between two layers of gas-impermeable material 38. A hole 44 that corresponds to the insert 36 is cut in each of the layers of gas-impermeable material 38 and allows gaseous sterilant to pass through the insert 36. In FIG. 6B, the flexible cover 28' includes a single layer of gas-impermeable material 38. The insert 36 is arranged to cover a hole 44 formed in the gas-impermeable material 38. The insert 36 is bonded to the gas-impermeable material 38 along the peripheral edge 40 at a seam 46. The seam 46 can include an adhesive that adheres the insert 36 to the gas-impermeable material 38.

Figure 7:
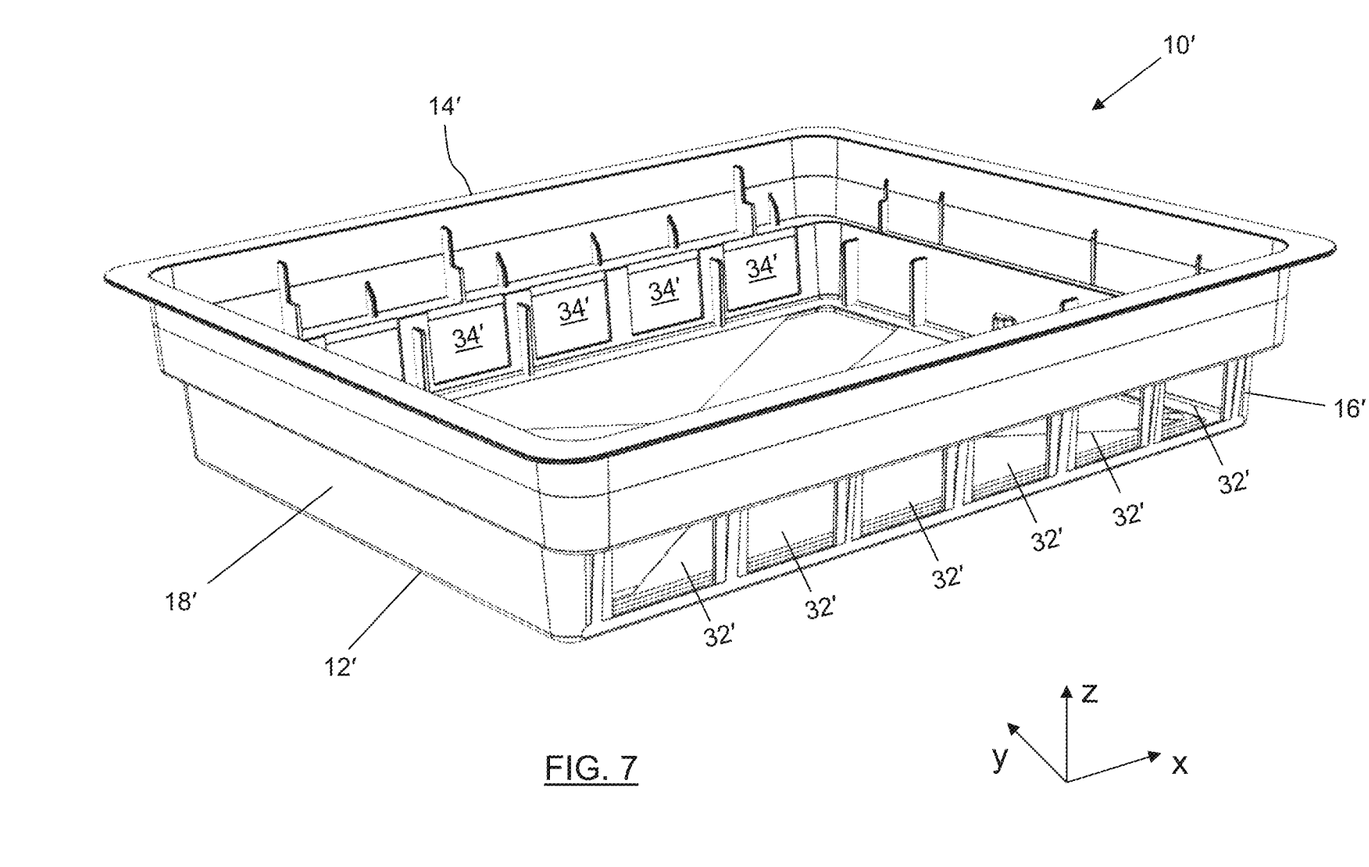
FIGS. 7 and 8 show a further example of a body for a container according to the present disclosure.
Figure 8:
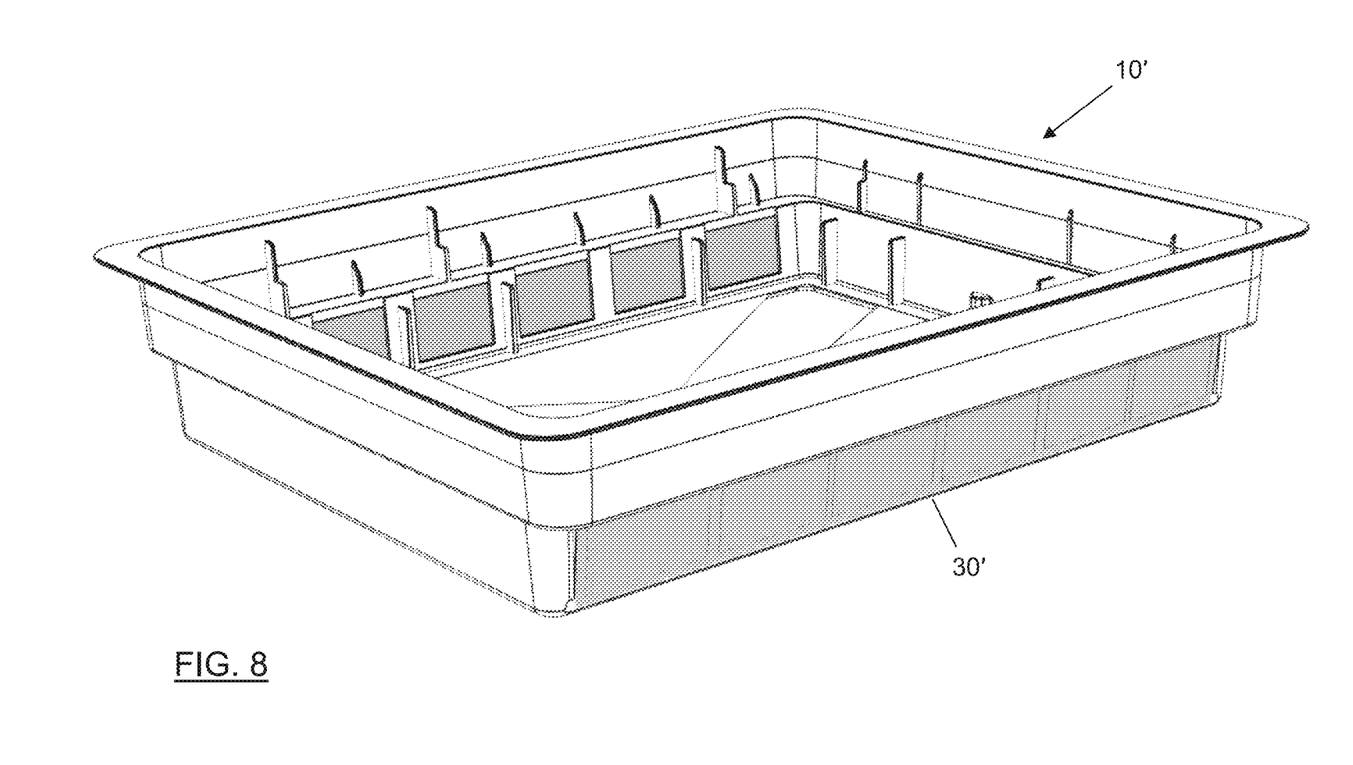

FIGS. 7 and 8 show a further body 10' for a container 100 according to the present disclosure. The body 10' includes a lower surface 12', an upper rim 14', and two pairs of side walls 16', 18'. The body 10' has substantially the same design as the body 10 of FIGS. 1 to 4. However, the body 10' has a smaller height along the Z-axis and a longer length along the X-axis than the body 10. Given this difference in dimensions, the long side walls 16' are provided with six pairs of apertures 32', 34' that are covered by gas-permeable material 30 (FIG. 8). Generally speaking, the greater size and/or the number of apertures, the shorter the duration of the sterilization cycles. To this end, the body 10' of FIGS. 7 and 8 can also be provided with one or more apertures in the lower surface 12' or the short side walls 18'. A flexible cover (not shown) that includes one or more inserts of gas-permeable material can be bonded to the upper rim 14'.

Figure 9:
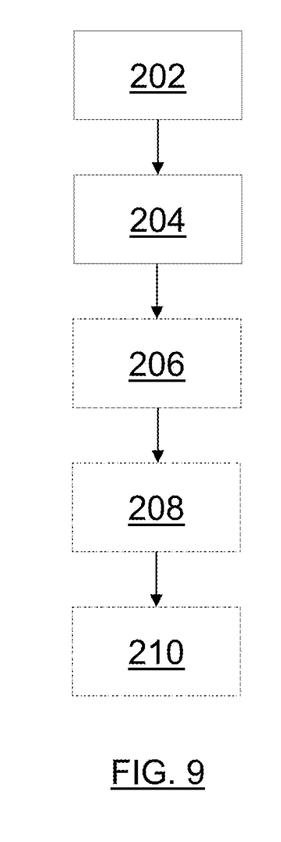
FIG. 9 shows a schematic flowchart of a method according to the present disclosure.

FIG. 9 is a schematic flowchart of a method 200 according to the present disclosure. The method 200 includes receiving 202 a body that includes a lower surface, an upper rim, and a plurality of side walls that extend between the lower surface and the upper rim, wherein the upper rim defines an opening to an interior space of the body, and wherein one of the plurality of side walls includes one or more apertures that extend through the side wall and/or the lower surface includes one or more apertures that extend through the lower surface. For instance, the body may be the body 10 shown in FIG. 1 or the body 10' shown in FIG. 7.

The method 200 further includes covering 204 the one or more apertures with a gas-permeable material, e.g., as shown in FIGS. 2 and 8. As described above, the gas-permeable material can include a gas-permeable foil, such as Tyvek®. In some instances, the method 200 begins with an injection molded body and attaches the gas-permeable material to the injection molded body. For example, the gas-permeable material can be cut to size and placed over the one or more of the apertures. A heat stamp can be applied to the gas-permeable material while an opposite surface of the injection molded body is held in place by a counter holder. Alternatively, the gas-permeable material can be bonded to an inner surface of the body, i.e., to a surface that faces the interior space of the body.

In yet a further alternative, covering 204 the one or more apertures with a gas-permeable material can take place at the same time the body is manufactured. For example, the body may be formed by injection molding, and the gas-permeable material can be attached to cover the one or more apertures during the injection molding process. Suitable processes for attaching the gas-permeable material in this way can include overmolding or insert molding.

The method 200 can optionally include loading 206 a plurality of vials, ampoules, cartridges, or syringe bodies in corresponding recesses of a support tray, arranging 208 the loaded support tray in the interior space of the body, and bonding 210 a flexible cover to the body along the upper rim of the body.

The flexible cover can be the flexible cover 28, 28' shown in FIGS. 2 and 4 to 6, for example. In some instances, bonding 210 the flexible cover to the body along the upper rim of the body can include receiving a flexible cover made of gas-impermeable material that is sized to cover the opening to the interior space of the body, forming an opening in the gas-impermeable material, covering the opening in the gas-impermeable material with a gas-permeable insert, and bonding a peripheral edge of the gas-impermeable material to the upper rim of the body. The flexible cover can be formed as shown in FIG. 6A. A second layer of gas-impermeable material can be arranged over the gas-permeable insert and the first layer of gas-impermeable material described above. The second layer of gas-impermeable material includes an opening aligned with the gas-permeable insert. The gas-permeable insert can then be laminated between the first and second layers of gas-impermeable material. Alternatively, the flexible cover can be formed as shown in FIG. 6B by adhering a peripheral edge of the gas-permeable insert to the gas-impermeable material using an adhesive.

A number of embodiments have been described. Nevertheless, numerous alternative embodiments within the scope of the claims will be readily appreciated by those skilled in the art. The presently described embodiments are not to be taken as limiting the scope of the invention.

The invention claimed is:

1. A container comprising:
   a body that comprises a lower surface, an upper rim, and a plurality of side walls that extend between the lower surface and the upper rim, wherein the upper rim defines an opening to an interior space of the body, at least one side wall of the plurality of side walls comprises one or more first apertures that extend through the at least one side wall, and the lower surface comprises one or more bottom apertures that extend through the lower surface;
   a flexible cover that covers the opening of the body and is bonded to the body along the upper rim, the flexible cover comprising an insert formed in the flexible cover and a gas-impermeable material that encircles the insert, the insert comprising a first gas-permeable material through which gas can enter and exit the interior space of the body; and
   a second gas-permeable material connected to the body and covering the one or more first apertures and the one or more bottom apertures, wherein gas can enter and exit the interior space of the body through the second gas-permeable material,
   wherein the upper rim of the body is spaced apart from any of the first gas-permeable material and the second gas-permeable material, such that the cover can be peeled away from the upper rim to expose the opening while leaving the first and second gas-permeable materials intact.

2. The container according to claim 1, wherein a first side wall of the plurality of side walls comprises the one or more first apertures that extend through the first side wall and that are covered by the second gas-permeable material, wherein a second side wall of the plurality of side walls opposite to the first side wall comprises one or more second apertures that extend through the second side wall and that are covered by the second gas-permeable material.

3. The container according to claim 1, wherein the body is configured to receive a support tray arranged in the interior space of the body, wherein the support tray is of a type comprising an array of recesses, each recess configured to receive a vial, ampoule, cartridge, or syringe body, wherein the support tray is sized to fit through the opening of the body.

4. The container according to claim 1, wherein at least one bottom aperture of the one or more bottom apertures is aligned with the insert formed in the flexible cover.

5. The container according to claim 1, wherein the flexible cover comprises two overlapping layers of the gas-impermeable material and a hole through the two overlapping layers, wherein the insert comprising the first gas-permeable material is laminated between the overlapping layers of the gas-impermeable material, and the insert covers the hole.

* * * * *